United States Patent [19]
Kellett et al.

[11] Patent Number: 5,001,424
[45] Date of Patent: Mar. 19, 1991

[54] APPARATUS FOR MEASURING MAGNETIC PARTICLES SUSPENDED IN A FLUID BASED ON FLUCTUATIONS IN AN INDUCED VOLTAGE

[75] Inventors: I. Peter Kellett, Wenham; John R. Erickson, Salem, both of Mass.

[73] Assignee: Product Resources, Inc., Wakefield, Mass.

[21] Appl. No.: 306,805

[22] Filed: Feb. 3, 1989

[51] Int. Cl.$^5$ .................. G01N 27/74; G01R 33/12
[52] U.S. Cl. .......................... 324/204; 73/64; 340/631
[58] Field of Search ............ 324/204, 235, 71.1, 324/71.4, 225, 226, 227, 262; 73/53, 61 R, 64; 340/627, 631

[56] References Cited

U.S. PATENT DOCUMENTS

| | | | |
|---|---|---|---|
| 2,215,605 | 9/1940 | DeLanty | 324/225 |
| 3,231,815 | 1/1986 | Spencer | 324/61 |
| 3,433,057 | 3/1969 | Halsey | 324/204 X |
| 3,676,773 | 7/1972 | Eckhardt | 324/228 |
| 3,748,576 | 7/1973 | Sigournay | 324/41 |
| 4,100,491 | 7/1978 | Newman et al. | 324/204 |
| 4,144,741 | 3/1979 | Nakamoto et al. | 324/204 X |
| 4,176,545 | 12/1979 | Oddo | 73/64 |
| 4,219,805 | 8/1980 | Magee et al. | 340/631 |
| 4,563,644 | 1/1986 | Lenander et al. | 324/264 X |
| 4,651,091 | 3/1987 | Chambers et al. | 324/204 |
| 4,651,092 | 3/1987 | Brunsch et al. | 324/204 |
| 4,692,698 | 9/1987 | Lewis | 324/204 |
| 4,731,578 | 3/1988 | Tsaprazis | 324/204 |
| 4,766,373 | 8/1988 | Chambers et al. | 324/204 |
| 4,785,239 | 11/1988 | Brunsch et al. | 324/204 |

FOREIGN PATENT DOCUMENTS

| | | |
|---|---|---|
| 751242 | 6/1970 | France . |
| WO85/04715 | 10/1985 | PCT Int'l Appl. . |
| 2101330 | 1/1983 | United Kingdom . |
| 2190503 | 11/1987 | United Kingdom . |

Primary Examiner—Reinhard J. Eisenzopf
Assistant Examiner—Warren S. Edmonds
Attorney, Agent, or Firm—Fish & Richardson

[57] ABSTRACT

An apparatus for detecting magnetic particles suspended in a liquid, such as particles suspended in lubricating oil flowing through an engine. The oil is caused to pass through the area coupling two or more coils while the mutual inductance of the coils is monitored. When a magnetic particle enters the area coupling the coils, the mutual inductance of the coils will increase, thereby indicating the presence of the particle.

23 Claims, 3 Drawing Sheets

APPARATUS FOR MEASURING MAGNETIC PARTICLES SUSPENDED IN A FLUID BASED ON FLUCTUATIONS IN AN INDUCED VOLTAGE

BACKGROUND OF THE INVENTION

This invention relates to the detection of suspended particulate matter in a liquid, and particularly to particles of magnetic material suspended in lubricating fluid.

In engines and other machinery, early warning of potential failure of bearings or other lubricated components can prevent the machine's ultimate failure through replacing or servicing the failing component. This becomes particularly significant when aircraft engines and the like are considered where an engine failure can have disastrous consequences.

When a lubricated engine component begins to deteriorate, small particles of the component are dislodged and carried away in lubricating fluid such as oil that flows around the component. As the component becomes more worn, and therefore becomes more likely to fail, the dislodged particles become larger and more numerous. The detection of such particles in the lubricating fluid provides an indication of the condition of the engine. By monitoring the size and number of such particles, imminent engine failure can be predicted and thereby avoided.

One well known method of detection relies upon the entrapment of particles by a magnetic device. The magnetic device is typically placed in the system that circulates the lubricating fluid, such that the fluid passes in close proximity to the magnetic device. Particles in the fluid are usually derived from metal components, and will therefore be magnetic particles (i.e., particles capable of being magnetized). Therefore, the particles will be attracted to, and trapped by, the magnetic device.

In some cases the magnetic device is physically examined on a periodic basis to determine the quantity and size of the trapped particles. In other cases, the magnetic device generates an electrical signal after a certain accumulation of particles has occurred. Still other methods of detection generate an electrical signal each time a particle is trapped. The electrical signal is typically generated through a measurement of the self inductance of a magnetic coil placed in close proximity to the magnetic device, where the self-inductance of the coil is a function of the quantity and size of magnetic particles deposited on the magnetic device.

Another device for detecting magnetic particles uses a coil wrapped around a tube through which the lubricating fluid is passed. The self inductance of the coil is closely monitored. When a magnetic particle passes through the tube, and therefore through the center of the coil, the self-inductance of the coil will increase slightly in proportion to the size of the particle.

SUMMARY OF THE INVENTION

The invention generally features an apparatus for detecting magnetic particles suspended in a liquid, the apparatus comprising: a source of an electrical signal; a first coil connected to the electrical signal source; a second coil coupled to the first coil such that the first coil induces a voltage in the second coil, the second coil having an output; a conduit for passing the liquid through the region coupling the first and second coils; and an electrical signal processor connected to the output of the second coil; wherein the electrical signal processor indicates the presence of magnetic particles in the liquid based on the induced voltage.

In a first embodiment of the invention, the apparatus includes a third coil coupled to the second coil, the third coil also being connected to the electrical signal source such that the third coil also induces a voltage in the second coil. The electrical signal processor will process the voltage induced by both the first coil and the second coil. The first and third coils are preferably connected together in series.

The conduit includes a non permeable tube with each of the coils being wound around the tube such that a liquid passes through the center of each coil. In the first embodiment, the first and third coils are wound around the tube in opposite directions.

In a second embodiment of the invention, the third coil is connected in series to the second coil and coupled to the first coil such that the first coil induces a voltage in both the second coil and the third coil. In this embodiment, the second and third coils are wrapped around the tube in opposite directions. The electrical signal processor processes the voltage across both the second coil and the third coil to detect magnetic particles.

In the first embodiment, the voltage induced in the second coil by the first coil is out of phase with the voltage induced in the second coil by the third coil. In the second embodiment, the voltage induced in the second coil is out of phase with the voltage induced in the third coil.

In both the first and second embodiments, the magnitude of the voltage induced from one coil to another coil increases when a magnetic particle is located in the region coupling the two coils, the size of the voltage increase being indicative of the mass of the particle. In the preferred embodiments, the electrical signal is a sinusoid of a predetermined frequency.

In a third embodiment of the invention, the electrical signal source is connected to the electrical signal processor.

The invention also generally features a method for detecting magnetic particles suspended in a liquid comprising the steps of: energizing a first coil with an electrical signal to induce a voltage in a second coil coupled to the first coil; passing the liquid through the region coupling the coils; and processing the voltage induced in the second coil, the voltage indicating the presence of magnetic particles in the liquid.

The present invention is a significant improvement over prior art systems for detecting magnetic particles. Unlike prior art systems, the present invention detects particles by detecting a change in the mutual inductance of a plurality of coils. A magnetic particle passing between two coils will increase their mutual inductance. Since one coil is energized by an electrical signal and the induced voltage in the second coil is monitored, this increase in mutual inductance will generate a measurable increase in the induced voltage at the same frequency as the signal source. The frequency component of this signal makes it easily distinguishable from background noise, allowing background noise to be filtered and eliminated before or during amplification. When three coils are used, as described more fully below, two distinct signals are generated for each particle that passes through the tube. The two signals are generated by magnetic fields of opposite polarities and will therefore be out of phase with one another, further improving the accuracy of particle detection.

The prior art systems discussed above that rely on changes in self inductance do not produce a detection signal having a frequency component, making it difficult to distinguish the detection signal from background noise. As a result, noise will be amplified with the detection signal resulting in poor signal quality. As discussed above, the present invention produces a detection signal with a frequency component. Accordingly, the present invention will detect small particles that would go undetected in prior art systems. The high quality detection signal of the present invention can also accurately measure the mass of detected particles, providing an indication a to the condition of the machine being monitored. Furthermore, as discussed more fully below, a preferred embodiment will produce two distinct detection signals for each detected magnetic particle, further increasing the accuracy of the invention.

DETAILED DESCRIPTION OF THE PREFERRED EMBODIMENTS

STRUCTURE

Figure 1:
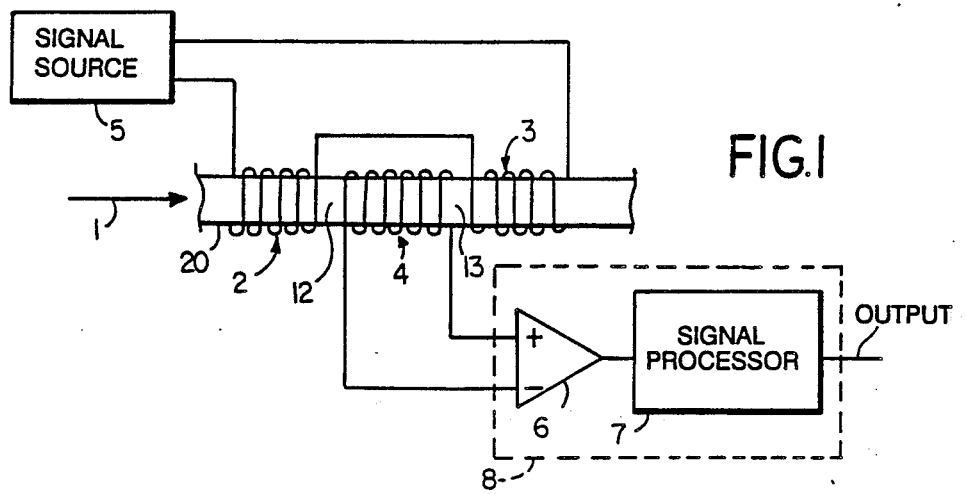
FIG. 1 is a block diagram of a magnetic particle detector according to a first embodiment of the invention.

Referring to FIG. 1, the particle detector includes three coils or windings 2, 3, 4 which are wound around non permeable tube 20 through which lubricating fluid from an engine or other machine flows in the direction designated by arrow 1. Coils 2, 3 are energized by signal source 5. The outputs of coil 4 are connected to detection mechanism 8 which includes amplifier 6 and signal processor 7 having an output that is provided to a suitable device such as a computer or warning light, etc. (not shown).

Figure 2:
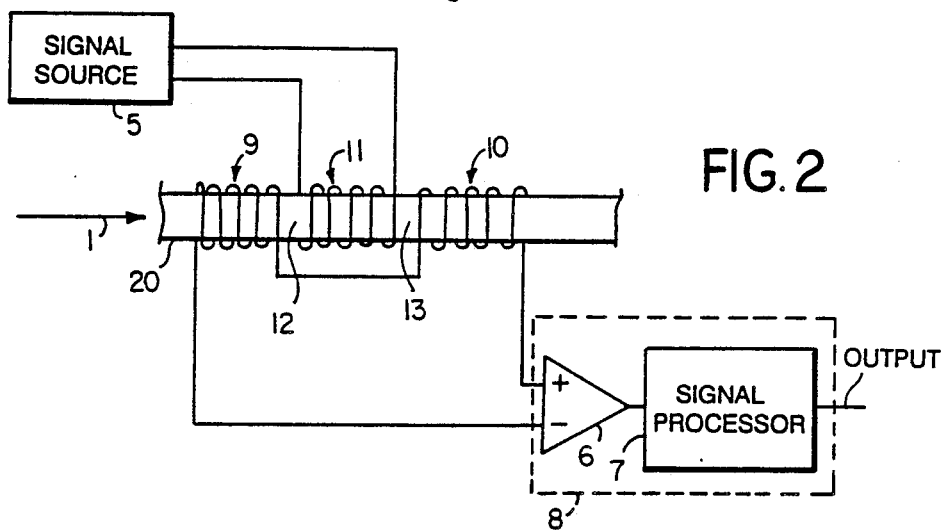
FIG. 2 is a block diagram of a second embodiment of the invention.

Referring to FIG. 2, a second embodiment of the detector includes coils 9, 10, 11 which are wound around non-permeable tube 20 through which lubricating fluid flows in the direction designated by arrow 1. Coil 11 is energized by signal source 5. The outputs of coils 9, 10 are connected to detection mechanism 8 which includes amplifier 6 and signal processor 7.

Figure 3:
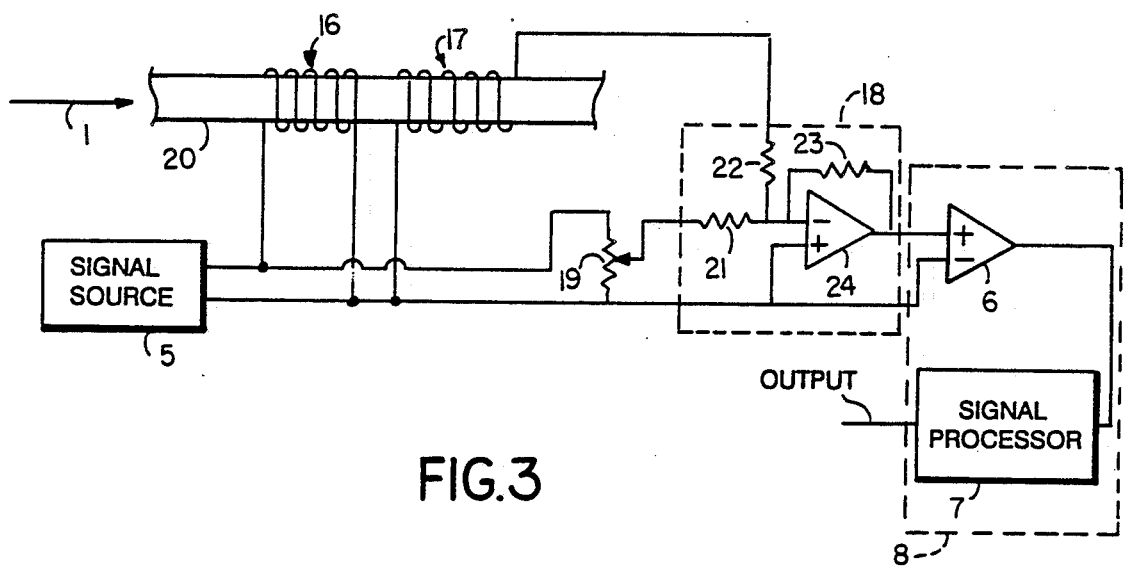
FIG. 3 is a block diagram of a third embodiment of the invention.

Referring to FIG. 3, a third embodiment of the invention includes coils 16, 17 wound around non-permeable tube 20 through which lubricating fluid flows in the direction designated by arrow 1. Coil 16 is energized by signal source 5. One terminal of coil 17 is connected to signal source 5 and the other terminal of coil 17 also connected to an input of summation amplifier 18. Summation amplifier 18 includes resistors 21, 22, 23 and amplifier 24. Signal source 5 is connected to the terminals of potentiometer 19. The wiper of potentiometer 19 is connected to a second terminal of summation amplifier 18. The output of summation amplifier 18 is connected to the input of detection mechanism 8. The detection mechanism includes amplifier 6 and signal processor 7.

The magnetic particle detector is preferably installed in close proximity to the monitored machine so that the lubricating oil can be arranged to pass through non permeable tube 20 without significantly disturbing the normal course of the oil's circulation. Tube 20 should be positioned so that the oil passes through it after it has passed through the machine but before it is filtered.

Operation

Referring to FIG. 1, signal source 5 causes an alternating current (e.g., a sinusoid) of known frequency to flow in coils 2, 3. The proximity of coil 4 to coils 2, 3 is such that the mutual inductance between the coils causes a voltage to be induced in coil 4 by each of coils 2, 3.

The amplitude of each induced voltage is a function of the ratio of the number of turns or windings in the primary coil (i.e., the coil connected to the signal source) to the number of turns in the secondary coil (i.e., the coil in which voltage is induced). This ratio is known as the "turns ratio."

The physical dimensions of the coils, e.g., the distance separating the coils, also effects the amplitude of the induced voltages. When the secondary coil is closer to the primary coil, the induced voltage is greater.

The amplitude of the induced voltage is also a function of the permeability of the material coupling the two coils. This is usually the material located between the coils. The permeability of a substance can approximately be defined as a property of the substance that determines it ability to concentrate a magnetic field. Since voltage is induced in a secondary coil by a primary coil through a coupled magnetic field created by current in the primary coil, the more permeable the material coupling the two coils, the more the magnetic field will be concentrated, and the more the field will be coupled to the secondary coil. Therefore, the higher the permeability of the substance coupling the two coils, the higher the amplitude of the induced voltage.

Coils 2, 3 each have the same number of windings such that the turns ratio between coil 2 and coil 4 is the same as the turns ratio between coil 3 and coil 4. Additionally, the physical dimensions of the coils will be the same. Finally, the material in area 12 between coil 2 and coil 4 will normally have the same permeability as the material in area 13 between coil 3 and coil 4 since the same material (i.e., tube 20 and its contained fluid) will be in each of those areas. Therefore, the amplitude of the voltage induced in coil 4 by coil 2 will normally be approximately equal to the amplitude of the voltage induced in coil 4 by coil 3.

Figure 4A:
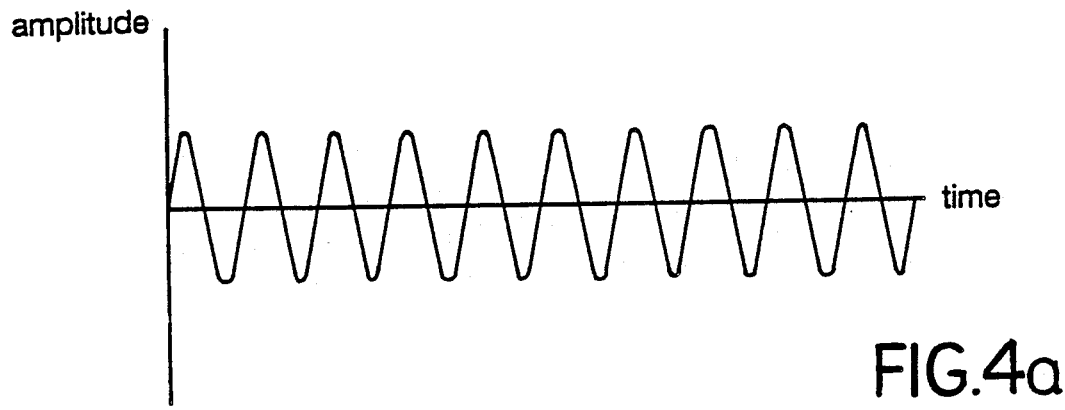
FIGS. 4 and 5 are sketches of voltage v. time, which illustrate electrical signals generated by the magnetic particle detector shown in FIGS. 1-2.
Figure 4B:
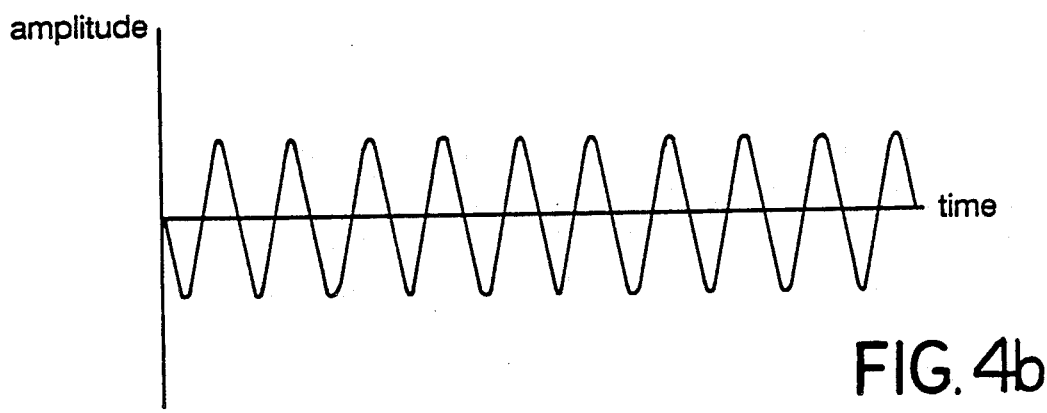
Figure 4C:
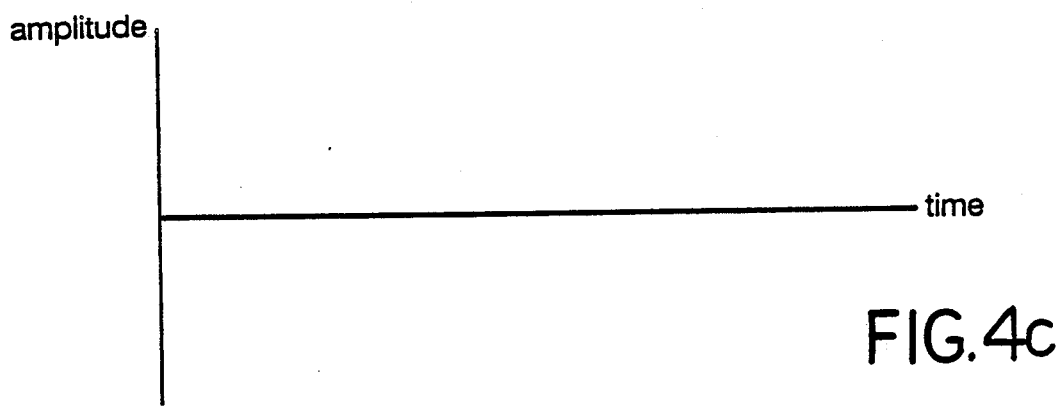

However, the polarity of the induced voltages will be opposite since coils 2, 3 are wound around tube 20 in opposite directions creating magnetic fields of opposite polarities. FIG. 4(A) illustrates the voltage induced in coil 4 by coil 2. and FIG. 4(B) illustrates the voltage induced in coil 4 by coil 3. (The amplitude of the voltages are shown as a function of time.) Therefore, at any given moment in time, coil 2 will induce a voltage in coil 4 that is approximately equal in magnitude and opposite in polarity to the voltage induced in coil 4 by coil 3. The resulting total voltage in coil 4 is shown in FIG. 4(C) and is equal to the sum of the voltages shown in FIGS. 4(A) and 4(B), and is approximately equal to zero at all times.

If a magnetic particle suspended in the lubricating fluid enters tube 20, it will pass through the center of coil 2 and enter area 12 beween coil 2 and coil 4. While the particle is in area 12, the permeability of area 12 will slightly increase since the particle will be a highly permeable substance such as steel or iron, thereby increasing the mutual coupling or mutual inductance between coil 2 and coil 4. As a result, the amplitude of the voltage induced in coil 4 by coil 2 will be greater during the time that the particle passes through area 12. Similarly, as the particle passes through area 13 between coils 3, 4, the mutual inductance between coil 3 and coil 4 will be increased, thereby increasing the amplitude of the voltage induced in coil 4 by coil 3.

Figure 5A:
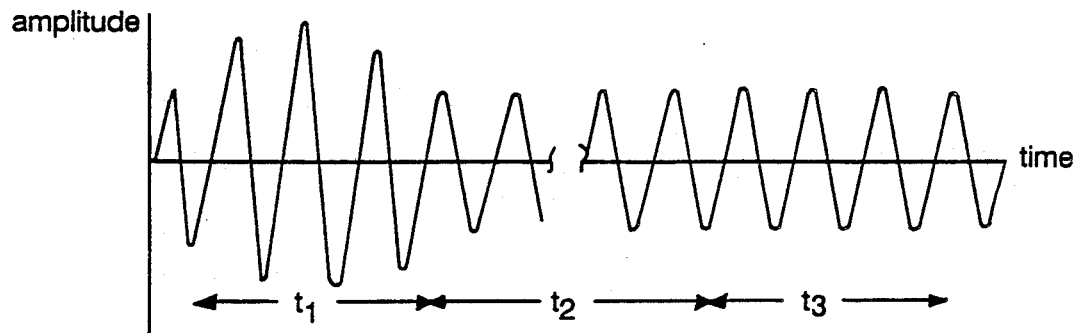

FIG. 5(A) illustrates the voltage induced in coil 4 by coil 2 as a magnetic particle passes through tube 20. The time period represented by $t_1$ indicates the time that the particle is in area 12 between coils 2, 4. Time $t_2$ is the time that the particle is between areas 12 and 13. (Note that a portion of the sketch in the middle of $t_2$ has been removed due to space limitations since $t_2$ is usually greater than $t_1$.) Time $t_3$ is the time when the particle is in area 13 between coils 3, 4. As can be seen in FIG. 5(A), when the particle is in area 12 (i.e., during $t_1$) the amplitude of the voltage induced in coil 4 by coil 2 increases due to the increased mutual inductance between coils 2,4. During times $t_2$ and $t_3$, the amplitude of the voltage induced by coil 2 is unchanged (i.e., is the same as shown in FIG. 4(A)). Therefore, the presence of the particle in area 12 increases the ability of coil 2 to induce voltage in coil 4. Once the particle moves along tube 20 away from area 12, the amplitude of the voltage induced by coil 2 returns to its previous value.

Figure 5B:
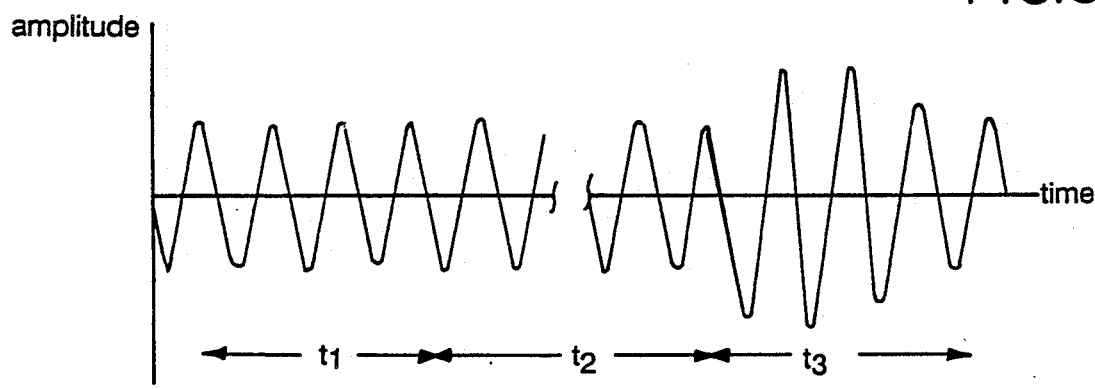

FIG. 5(B) illustrates the voltage induced in coil 4 by coil 3. A similar effect is observed when the particle is in area 13 (i.e., during time $t_3$), with the amplitude of the induced voltage being increased.

Figure 5C:
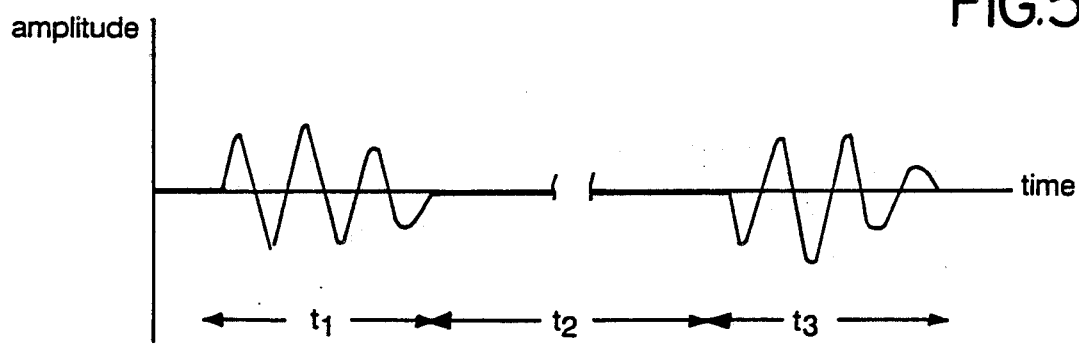

FIG. 5(C) illustrates the resulting total voltage in coil 4, which is the sum of the voltages shown in FIGS. 5(A) and 5(B). Unlike the case illustrated in FIG. 4, when a magnetic particle passes through tube 20 the total voltage in coil 4 will not be zero at all times. Two distinct signals or pulses will be seen which correspond to the time intervals when the particle is in each of areas 12, 13. These two pulses will be at the same frequency as the input signal from signal source 5 and will be 180° out of phase with respect to each other (because the signals in FIGS. 5(A) and 5(B) are 180° out of phase).

Accordingly, each time a magnetic particle passes through tube 20, two distinct pulses will be detected by detection mechanism 8. Amplifier 6 will amplify the pulses and feed the signal to signal processor 7. Signal processor 7 can easily distinguish the pulses from background noise due to their frequency component (i.e., through standard filtering techniques). Note that it may be desirable to filter the signal before it is amplified by amplifier 6 to avoid amplifying noise. Signal processor 7 will also compare the detected pulses to ensure that they are 180° out of phase. The detection of two consecutive, out of phase pulses will provide absolute assurance of the detection of a particle. The magnitude of the pulses are measured to provide an indication as to the mass of the particle. The output of signal processor 7 can be provided to a warning indicator, e.g., a warning light in the cockpit of an aircraft. Alternatively, the output can be provided to a computer that evaluates the condition of the device based on the number and size of the detected particles.

Referring to FIG. 2, in the second embodiment of the invention the primary and secondary windings of the mutually coupled coils of FIG. 1 have been exchanged. Signal source 5 now energizes a single primary coil 11 that will induce a voltage in secondary coils 9, 10 which are connected to detection mechanism 8.

The same phenomenon discussed above will result with the embodiment of FIG. 2. Since coils 9, 10 are wound around tube 20 in opposite directions, coil 11 will induce voltages of equal amplitude in each but 180° out of phase (i.e., the same as the voltages illustrated in FIGS. 4(A) and 4(B)). Since coils 9, 10 are connected together in series, the voltage supplied to detection mechanism 8 will be the sum of the induced voltages, which will be approximately equal to zero at all times under normal conditions (see FIG. 4(C)).

A magnetic particle passing through tube 20 of the FIG. 2 embodiment will be detected in the same manner as discussed above with respect to the FIG. 1 embodiment. As the particle passes through areas 12, 13, the total voltage across coils 9, 10 will not be zero and two pulses will be detected by detection mechanism 8 (see FIG. 5).

In the first two embodiments described above, it may be difficult to make the voltages induced in the secondary coils cancel each other out exactly. Therefore, one secondary coil may be arranged to have a higher output than the other and the resulting constant amplitude output signal compensated in signal processor 7.

Referring to FIG. 3, there is shown a third embodiment of the invention. Sensing coil 17 is connected to a standard summation amplifier 18 where the summation amplifier subtracts a signal derived from signal source 15 from the output of coil 17 thereby producing steady state cancellation effect without the addition of a third coil. In other words, instead of having two induced voltages that cancel one another out as in the embodiments of FIGS. 1 and 2, the embodiment of FIG. 3 uses a signal derived from signal source 5 to cancel out the voltage induced in coil 17 by coil 16 under normal conditions (i.e., without a particle in the tube). Potentiometer 19 adjusts the gain of the signal source component so as to achieve a signal equal in magnitude to the signal induced in coil 17. The output of summation amplifier 18 is therefore zero during normal conditions. When a particle enters tube 20 and passes between coils 16,17, the output of coil 17 will increase and the output of amplifier 18 will have a pulse at the frequency of signal source 5. The pulse is amplified and detected by detection circuit 8 as described above.

Other embodiments of the invention are within the scope of the appended claims.

We claim:

1. A method for predicting the failure of a lubricated machine by detecting magnetic particles suspended in a liquid used to lubricate the machine, said method comprising the steps of:

energizing a first coil with an electrical signal to induce a voltage in a second coil coupled to said first coil;

passing said liquid through the region coupling said coils;

processing said voltage induced in said second coil to detect fluctuations in said voltage; and indicating the presence of magnetic particles in said liquid in response to said detected fluctuations to thereby predict whether said machine will fail.

2. The method of claim 1 wherein said machine is an engine.

3. The method of claim 1 wherein said step of processing further comprises processing said electrical signal.

4. The method of claim 1 wherein said step of passing comprises passing said liquid through a conduit.

5. The method of claim 4 wherein said coils are wound around said conduit, such that said liquid passes through each of said coils.

6. The method of claim 1 further comprising the step of energizing a third coil with an electrical signal, said third coil coupled to said second coil to thereby induce a second voltage in said second coil, wherein said step of passing further comprises passing said liquid through the region coupling said second coil and said third coil and wherein said step of processing further comprises processing said second voltage.

7. The method of claim 6 wherein said first coil and said third coil are connected together in series.

8. The method of claim 6 wherein said voltage induced in said second coil by said first coil is out of phase with said voltage induced in said second coil by said third coil.

9. The method of claim 8 wherein said step of indicating comprises indicating the presence of a magnetic particle if two of said fluctuations are detected, and if said two fluctuations are out of phase.

10. The method of claim 6 wherein said step of passing comprises passing said liquid through a conduit.

11. The method of claim 10 wherein each of said coils is wound around said conduit such that said liquid passes through each of said coils.

12. The method of claim 11 wherein said first coil and said third coil are wound around said conduit in opposite directions.

13. The method of claim 6 wherein each of said fluctuations comprises an increase in the magnitude of said induced voltage, said increase occurring when a magnetic particle is located in either the region coupling said first and second coils or the region coupling said second and third coils.

14. The method of claim 13 wherein said step of indicating comprises indicating the presence of a magnetic particle if two of said fluctuations are detected.

15. The method of claim 1 wherein said first coil further induces a voltage in a third coil coupled to said first coil, wherein said step of passing further includes passing said liquid through the region coupling said first coil and said third coil, and wherein said step of processing further includes processing said voltage induced in said third coil.

16. The method of claim 15 wherein said second coil and said third coil are connected together in series.

17. The method of claim 15 wherein said step of passing comprises passing said liquid through a conduit.

18. The method of claim 17 wherein each of said coils is wound around said conduit such that said liquid passes through each of said coils.

19. The method of claim 18 wherein said second coil and said third coil are wound around said conduit in opposite directions.

20. The method of claim 15 wherein each of said fluctuations comprises an increase in the magnitude of said induced voltage, said increase occurring when a magnetic particle is located in either the region coupling said first and second coils or the region coupling said second and third coils.

21. The method of claim 20 wherein said step of indicating comprises indicating the presence of a magnetic particle if two of said fluctuations are detected.

22. The method of claim 15 wherein said voltage induced in said second coil is out of phase with said voltage induced in said third coil.

23. The method of claim 22 wherein said step of indicating comprises indicating the presence of a magnetic particle if two of said fluctuations are detected, and if said two fluctuations are out of phase.

* * * * *